United States Patent
Deaton

(10) Patent No.: US 6,652,567 B1
(45) Date of Patent: Nov. 25, 2003

(54) FENESTRATED ENDOVASCULAR GRAFT

(76) Inventor: David H. Deaton, 1593 Piscataway Rd., Crownsville, MD (US) 21032

( * ) Notice: Subject to any disclaimer, the term of this patent is extended or adjusted under 35 U.S.C. 154(b) by 0 days.

(21) Appl. No.: 09/717,792

(22) Filed: Nov. 20, 2000

Related U.S. Application Data

(60) Provisional application No. 60/166,532, filed on Nov. 18, 1999.

(51) Int. Cl.$^7$ .................................................. A61F 2/06
(52) U.S. Cl. ...................... 623/1.1; 623/1.39; 623/1.11; 623/1.23
(58) Field of Search .............................. 623/1.11, 1.13, 623/1.14, 1.35, 1.39, 1.44, 1.1, 1.23, 903; 606/108

(56) References Cited

U.S. PATENT DOCUMENTS

| | | |
|---|---|---|
| 5,104,399 A | 4/1992 | Lazarus |
| 5,209,731 A | 5/1993 | Sterman et al. |
| 5,256,150 A | 10/1993 | Quiachon et al. |
| 5,395,349 A | 3/1995 | Quiachon et al. |
| 5,397,345 A | 3/1995 | Lazarus |
| 5,419,324 A | 5/1995 | Dillow |
| 5,484,418 A | 1/1996 | Quiachon et al. |
| 5,489,295 A | 2/1996 | Piplani et al. |
| 5,609,625 A | 3/1997 | Piplani et al. |
| 5,628,783 A | 5/1997 | Quiachon et al. |
| 5,653,697 A | 8/1997 | Quiachon et al. |
| 5,662,700 A | 9/1997 | Lazarus |
| 5,669,932 A | 9/1997 | Fischell et al. |
| 5,669,936 A | 9/1997 | Lazarus |
| 5,676,697 A * | 10/1997 | McDonald ............... 623/1.35 |
| 5,693,083 A | 12/1997 | Baker et al. |
| 5,697,971 A | 12/1997 | Fischell et al. |
| 5,723,004 A * | 3/1998 | Dereume et al. ......... 623/1.35 |
| 5,728,150 A * | 3/1998 | McDonald et al. ........ 623/1.15 |
| 5,749,920 A | 5/1998 | Quiachon et al. |
| 5,755,735 A * | 5/1998 | Richter et al. ............ 128/898 |
| 5,769,885 A | 6/1998 | Quiachon et al. |
| 5,782,909 A | 7/1998 | Quiachon et al. |
| 5,800,518 A | 9/1998 | Piplani et al. |
| 5,824,039 A | 10/1998 | Piplani et al. |
| 5,824,044 A | 10/1998 | Quiachon et al. |
| 5,855,600 A | 1/1999 | Alt |
| 5,910,144 A | 6/1999 | Hayashi |
| 5,935,122 A | 8/1999 | Fourkas et al. |
| 5,957,973 A | 9/1999 | Quiachon et al. |
| 5,961,548 A * | 10/1999 | Shmulewitz ............ 623/1.35 |
| 5,984,955 A * | 11/1999 | Wisselink ............... 623/1.35 |
| 6,210,429 B1 * | 4/2001 | Vardi et al. ............. 623/1.11 |
| 6,398,803 B1 * | 6/2002 | Layne et al. ............. 623/1.13 |

* cited by examiner

*Primary Examiner*—Paul B. Prebilic
(74) *Attorney, Agent, or Firm*—James J. Leary; Carol D. Titus

(57) ABSTRACT

A two-layered fenestrated vascular graft is provided for repair of diseased, damaged or aneurismal blood vessels. The fenestrated vascular graft is configured to be delivered transluminally and implanted within the lumen of a native blood vessel using catheter-based minimally-invasive surgical techniques. The vascular graft is fenestrated or perforated to facilitate making a fluid connection or anastomosis with one or more of the sidebranches of the vessel into which it is implanted. The vascular graft is adapted for implantation into blood vessels, such as the aorta, having tributary vessels or sidebranches along the section of the blood vessel to be repaired without occluding or obscuring the sidebranches. Methods are described for implanting the vascular graft into a patient's aorta for repairing thoracic or abdominal aortic aneurysms and for making a fluid connection or anastomosis with the tributary vessels or sidebranches of the aorta, such as the renal, hepatic and mesenteric arteries.

18 Claims, 9 Drawing Sheets

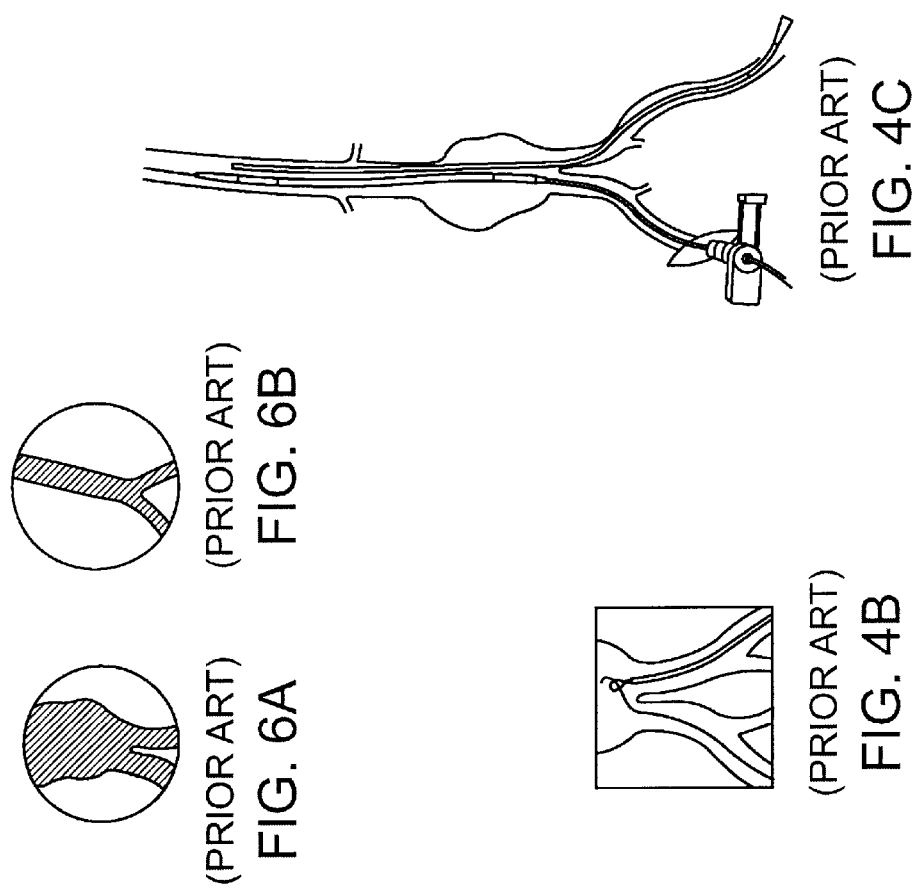
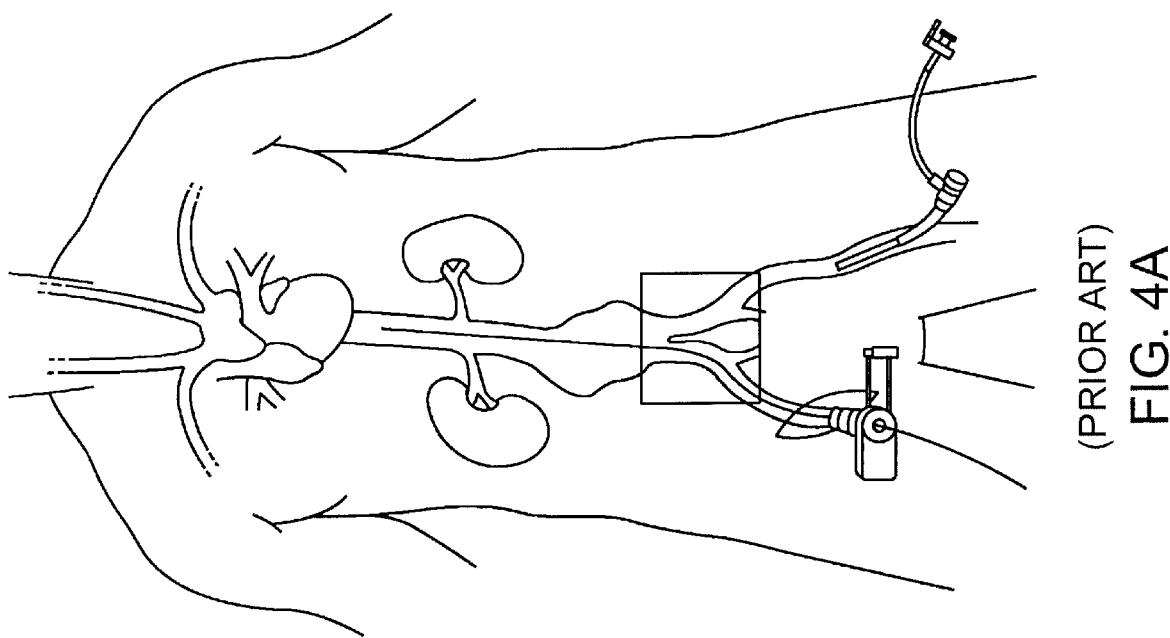

FENESTRATED ENDOVASCULAR GRAFT

This application claims benefits of Provisional application Ser. No. 60/166,532, filed Nov. 18, 1999.

FIELD OF THE INVENTION

The present invention relates generally to vascular grafts and prostheses for repair of damaged or aneurismal blood vessels. More particularly, it relates to a fenestrated endovascular graft for repair of blood vessels with tributary vessels or sidebranches and methods for placing the endovascular graft in the vessel and for making a fluid connection or anastomosis with one or more of the sidebranches.

BACKGROUND OF THE INVENTION

Vascular grafts or vascular prostheses are commonly used for repair of damaged or aneurismal blood vessels. Standard technique involves implanting a vascular graft into a patient to repair or replace a damaged or diseased section of the blood vessel using open surgical methods. The ends of the vascular graft are typically anastomosed to the blood vessel using sutures, surgical staples or clips. The native vessel may be removed or left in situ, depending on the surgical technique used and the nature of the damage or disease to the vessel. In recent years, techniques have been developed for implanting a vascular graft using minimally-invasive techniques in order to reduce the trauma of surgery. Typically, such vascular grafts are delivered transluminally and implanted within the lumen of the native blood vessel, hence they are often referred to as endovascular grafts, endoluminal grafts or endovascular prostheses. The ends of the endovascular graft are typically held in place by hooks, surgical staples or clips. Sometimes the ends of the endovascular graft and/or the body of the graft are supported by a stent or other reinforcement. A stent is a metallic and/or polymeric scaffold that holds the ends and/or the body of the graft in an open position. These grafts are typically referred to as stent-grafts or reinforced grafts. The stent or reinforcement may be self-expanding or an inflatable balloon or other expandable dilator may be used to expand the stent and/or the graft. The stent may also include anchoring hooks or clips to hold the stent-graft in place within the vessel. A common application for endovascular grafts of this sort is for repair of abdominal aortic aneurysms or AAA's. Depending on the location and extent of the disease, endovascular grafts for repair of abdominal aortic aneurysms may be straight for use in the abdominal descending aorta or they may be bifurcated for connecting from the descending aorta to the iliac or femoral arteries.

The following U.S. patents disclose bifurcated and non-bifurcated endovascular grafts for repair of abdominal aortic aneurysms and the like. These patents and all of the patents referred to therein are hereby incorporated by reference: U.S. Pat. No. 5,957,973 Multicapsule intraluminal grafting system and method; U.S. Pat. No. 5,935,122 Dual valve, flexible expandable sheath and method; U.S. Pat. No. 5,910,144 Prosthesis gripping system and method; U.S. Pat. No. 5,824,044 Bifurcated multicapsule intraluminal grafting system; U.S. Pat. No. 5,824,039 Endovascular graft having bifurcation and apparatus and method for deploying the same; U.S. Pat. No. 5,800,518 Method for deploying an endovascular graft having a bifurcation; U.S. Pat. No. 5,782,909 Multicapsule intraluminal grafting system and method; U.S. Pat. No. 5,769,885 Bifurcated multicapsule intraluminal grafting system and method; U.S. Pat. No. 5,749,920 Multicapsule intraluminal grafting system and method; U.S. Pat. No. 5,693,083 Thoracic graft and delivery catheter; U.S. Pat. No. 5,669,936 Endovascular grafting system and method for use therewith; U.S. Pat. No. 5,662,700 Artificial graft and implantation method; U.S. Pat. No. 5,653,697 Dual valve reinforced sheath and method; U.S. Pat. No. 5,628,783 Bifurcated multicapsule intraluminal grafting system and method; U.S. Pat. No. 5,609,625 Endovascular graft having bifurcation and apparatus and method for deploying the same; U.S. Pat. No. 5,489,295 Endovascular graft having bifurcation and apparatus and method for deploying the same; U.S. Pat. No. 5,484,418 Dual valve reinforced sheath and method; U.S. Pat. No. 5,419,324 Radiological marker board with movable indicators; U.S. Pat. No. 5,397,345 Artificial graft and implantation method; U.S. Pat. No. 5,395,349 Dual valve reinforced sheath and method; U.S. Pat. No. 5,256,150 Large-diameter expandable sheath and method; U.S. Pat. No. 5,209,731 Hand-held gun for inflating and aspirating large volume balloons; and U.S. Pat. No. 5,104,399 Artificial graft and implantation method.

While such endovascular grafts represent a significant step forward in the treatment of vascular disease, there remain technical and clinical challenges that the current graft technology does not address. In specific, known vascular grafts and endovascular grafts are not well adapted for implantation into vessels, such as the aorta, having tributary vessels or sidebranches along the section of the blood vessel to be repaired without occluding or obscuring the sidebranches. The present invention provides a technical solution for this previously unsolved clinical challenge.

SUMMARY OF THE INVENTION

In keeping with the foregoing discussion, the present invention takes the form of a vascular graft for repair of diseased, damaged or aneurismal blood vessels. In a particularly preferred embodiment, the vascular graft is in the form of an endovascular graft configured to be delivered transluminally and implanted within the lumen of a native blood vessel using catheter-based minimally-invasive surgical techniques. Preferably, the vascular graft is fenestrated or perforated to facilitate making a fluid connection or anastomosis with one or more of the sidebranches of the vessel into which it is implanted. Thus, the vascular graft of the present invention is adapted for implantation into blood vessels, such as the aorta, having tributary vessels or sidebranches along the section of the blood vessel to be repaired without occluding or obscuring the sidebranches.

Methods are described for implanting the vascular graft into a patient's aorta for repairing thoracic or abdominal aortic aneurysms and for making a fluid connection or anastomosis with the tributary vessels or sidebranches of the aorta, such as the renal, hepatic and mesenteric arteries.

BRIEF DESCRIPTION OF THE DRAWINGS

FIG. 3B shows an abdominal aortic aneurysm before implanting the endovascular graft. FIG. 3A shows the abdominal aortic aneurysm after repair by implanting the endovascular graft.

FIGS. 4A, 4B and 4C show a prior art bifurcated endovascular grafting system used for repair of an abdominal aortic aneurysm in a patient's aorta. FIGS. 4A and 4B show the steps for placing a lead wire for access to both femoral arteries. 4C shows the introduction of the bifurcated endovascular grafting system via one of the femoral arteries.

FIGS. 6A and 6B show angiograms of a patient's aorta. FIG. 6B shows an abdominal aortic aneurysm before implanting the bifurcated endovascular graft. FIG. 6A shows the abdominal aortic aneurysm after repair by implanting the bifurcated endovascular graft.

FIG. 7 shows a primary fenestrated endovascular graft constructed in accordance with the present invention for use in repairing abdominal aortic aneurysms or the like.

FIG. 12 shows a secondary fenestrated endovascular graft for use in conjunction with the primary fenestrated endovascular graft of FIG. 7 for use in repairing abdominal aortic aneurysms or the like.

DETAILED DESCRIPTION OF THE INVENTION

Figure 1:
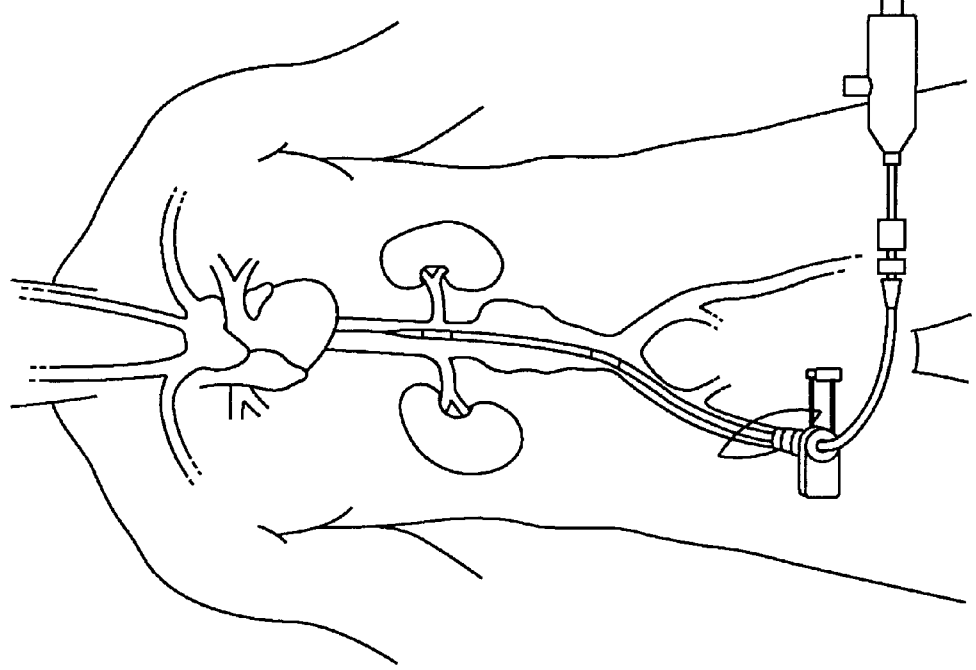
FIG. 1 shows a prior art endovascular grafting system used for repair of an abdominal aortic aneurysm in a patient's aorta.

FIG. 1 shows a prior art endovascular grafting system used for repair of an abdominal aortic aneurysm in a patient's aorta.

Figure 2:
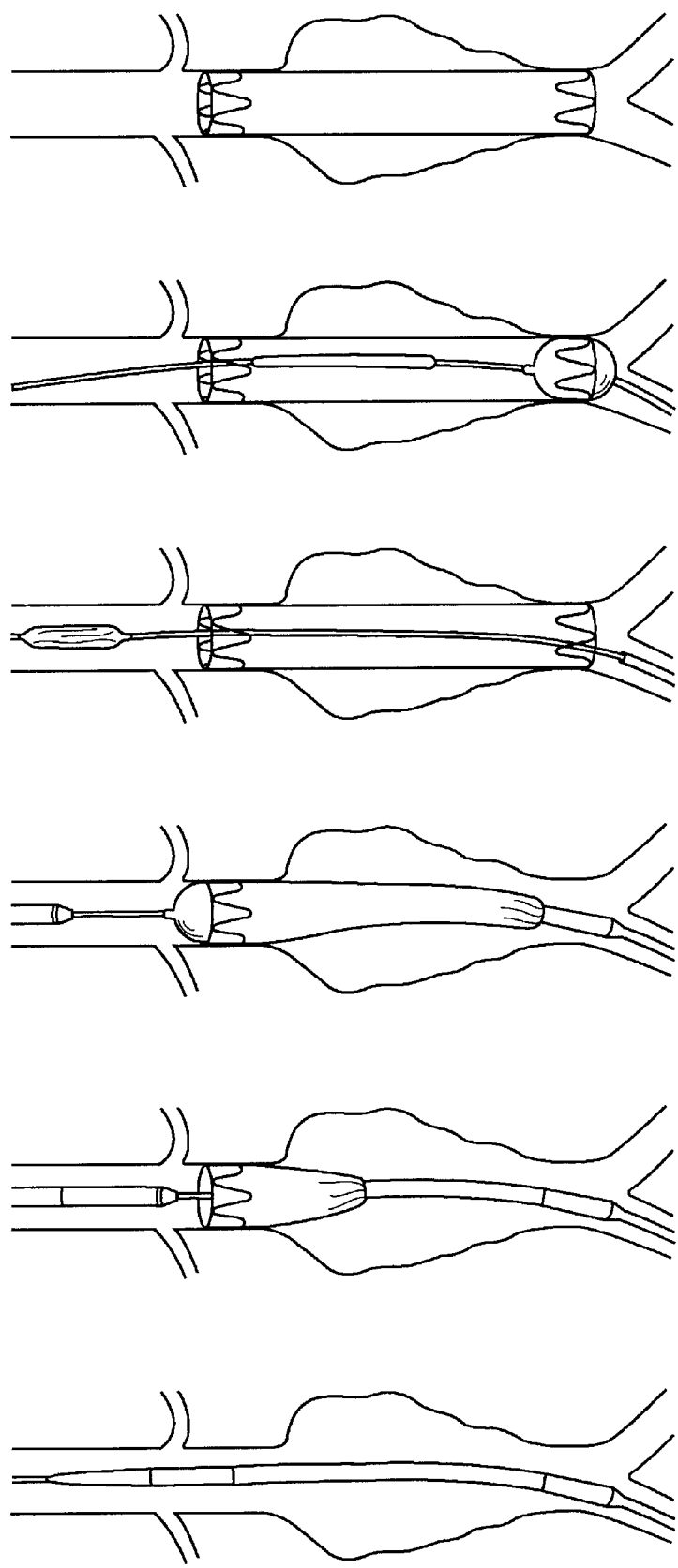
FIG. 2, steps 1–6, show a method of implanting a prior art endovascular graft in a patient's aorta to repair an abdominal aortic aneurysm.

FIG. 2, steps 1–6, show a method of implanting a prior art endovascular graft in a patient's aorta to repair an abdominal aortic aneurysm. In step 1, the endovascular graft is positioned within the patient's abdominal aorta. In step 2, the top attachment system of the endovascular graft is released. In step 3, a balloon is inflated to attach the top attachment system of the endovascular graft to the aortic wall. In step 4, the bottom attachment system of the endovascular graft is released. In step 5, a balloon is inflated to attach the bottom attachment system of the endovascular graft to the aortic wall. Step 6 shows the completed implantation of the endovascular graft within the abdominal aorta.

Figure 3A:
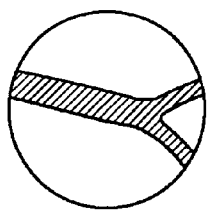
FIGS. 3A and 3B show angiograms of a patient's aorta.
Figure 3B:
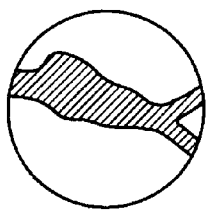

FIGS. 3A and 3B show angiograms of a patient's aorta. FIG. 3B shows an abdominal aortic aneurysm before implanting the endovascular graft. FIG. 3A shows the abdominal aortic aneurysm after repair by implanting the endovascular graft.

FIGS. 4A, 4B and 4C show a prior art bifurcated endovascular grafting system used for repair of an abdominal aortic aneurysm in a patient's aorta. FIGS. 4A and 4B show the steps for placing a lead wire for access to both femoral arteries. 4C shows the introduction of the bifurcated endovascular grafting system via one of the femoral arteries.

Figure 5:
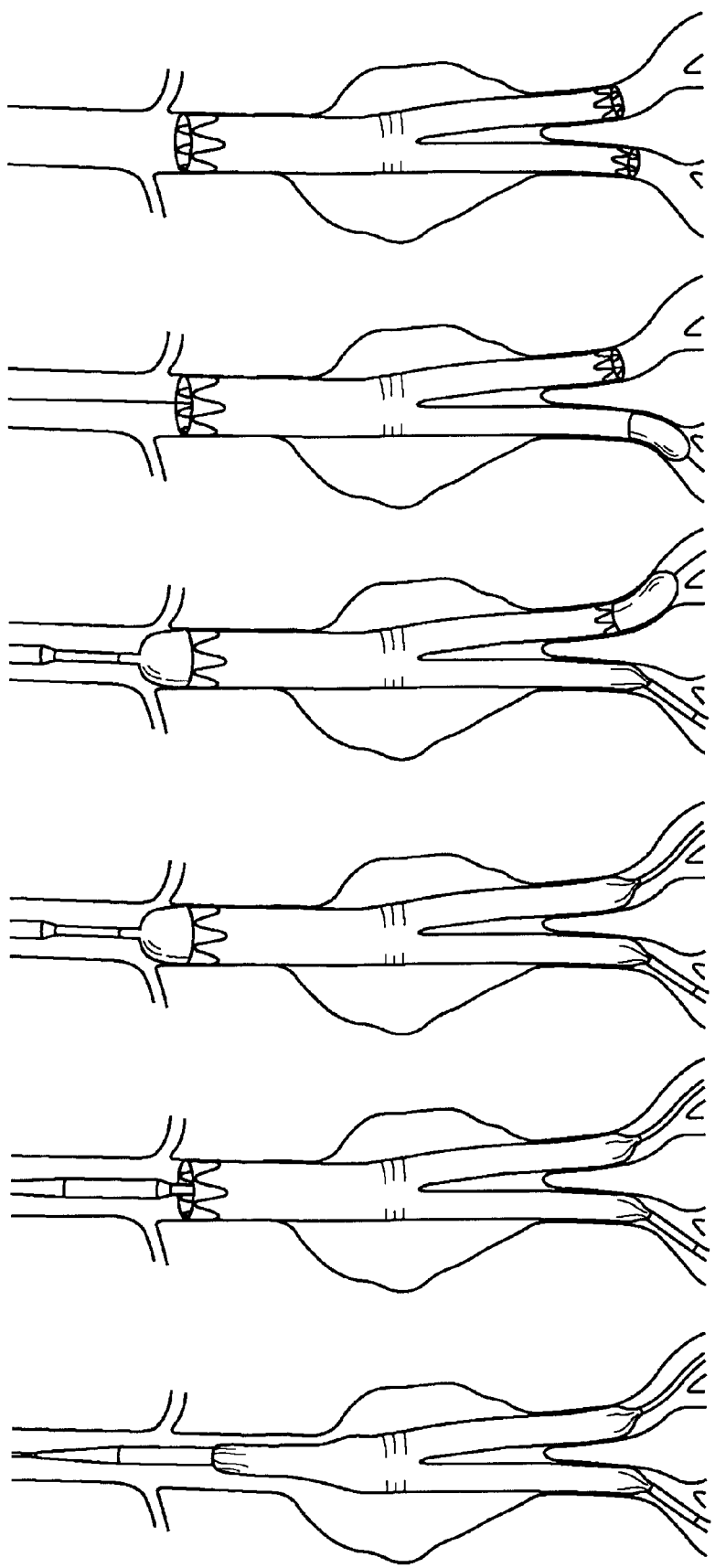
FIG. 5, steps 1–6, show a method of implanting a prior art bifurcated endovascular graft in a patient's aorta to repair an abdominal aortic aneurysm.

FIG. 5, steps 1–6, show a method of implanting a prior art bifurcated endovascular graft in a patient's aorta to repair an abdominal aortic aneurysm. In step 1, the lower limbs of the bifurcated endovascular graft are positioned within the patient's iliac arteries. In step 2, the top attachment system of the endovascular graft is released. In step 3, a balloon is inflated to attach the top attachment system of the endovascular graft to the aortic wall. In steps 4–5, the iliac attachment systems of the endovascular graft are released, and a balloon is inflated to attach the iliac attachment system of the endovascular graft to the iliac artery walls. Step 6 shows the completed implantation of the bifurcated endovascular graft within the abdominal aorta.

FIGS. 6A and 6B show angiograms of a patient's aorta. FIG. 6B shows an abdominal aortic aneurysm before implanting the bifurcated endovascular graft. FIG. 6A shows the abdominal aortic aneurysm after repair by implanting the bifurcated endovascular graft.

It is significant to note that in all of the above-referenced prior art disclosures, the superior or upstream end of the endovascular graft is always placed in an infrarenal position. It is contraindicated to place the end of the endovascular graft in a suprarenal position as this would occlude blood flow to the renal arteries, and possibly to the hepatic and mesenteric arteries as well. Occluding blood flow to any of these arteries would result in ischemia and necrosis of the affected organs and very likely death of the patient. For this reason, for a thoracic aortic aneurysm or an abdominal aortic aneurysm extending above any of these critical arteries, open surgery with a standard vascular graft must be used so that the graft can be anastomosed to each of the branch arteries.

Figure 7:
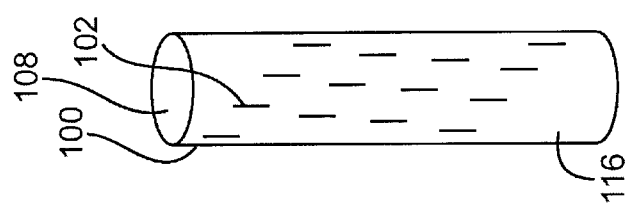

The present invention takes the form of an endovascular graft for use in repairing thoracic or abdominal aortic aneurysms or the like using catheter-based minimally-invasive surgical techniques. The endovascular graft consists of a primary fenestrated endovascular graft configured to be delivered transluminally and implanted within the lumen of a native blood vessel and, optionally, a secondary fenestrated endovascular graft configured to be implanted within the lumen of the primary fenestrated endovascular graft. FIG. 7 shows a first example of the primary fenestrated endovascular graft 100. The primary fenestrated endovascular graft 100 is generally tubular in shape with a central lumen 108. If desired, the primary fenestrated endovascular graft 100 may also be made in a bifurcated configuration, similar to that shown in FIGS. 4A–6B. The primary fenestrated endovascular graft 100 may be made of polyester, polytetrafluoroethylene (PTFE) or any other suitable fabric. The primary fenestrated endovascular graft 100 may be reinforced or unreinforced and stented or nonstented. The primary fenestrated endovascular graft 100 will have a multiplicity of fenestrations or perforations 102, which are preferably in the form of slits 2–15 mm long spaced at different intervals with either constant or varying distance between the slits. The slits 102 will be oriented longitudinally, horizontally (i.e. circumferentially) or at an angle with respect to the axis of the graft, or in any combination thereof. The perforations or slits 102 may pass all the way through the wall 116 of the primary fenestrated endovascular graft 100 or they may be thinner or weaker areas in the wall 116 to facilitate piercing the primary fenestrated endovascular graft 100. Alternatively, the primary fenestrated endovascular graft 100 may be made of a micromesh fabric with small holes that are guidewire accessible and dilatable.

Fixation of the primary fenestrated endovascular graft 100 may be accomplished with hooks, staples or clips or other suitable means known in the art. For example, the primary fenestrated endovascular graft 100 may be implanted using the methods described above in connection with steps 1–6 of FIG. 2 or FIG. 5. Fixation should be transmural in nature, either acutely or over a period of time, i.e. migration of fixation element transmurally. This prevents loosening of the attachment, which could result in extraluminal blood flow and/or collapse or migration of the graft.

The primary fenestrated endovascular graft 100 will be suitable for passage of guidewires, balloons, or other endovascular means of manipulation. It will serve as a scaffold for the placement of devices meant to access tributaries and/or provide a conduit to them. It will serve as a scaffold for other endovascular graft materials or prostheses to perform roles of reinforcement or provide further competence of graft sections between intervening tributaries.

Figure 8:
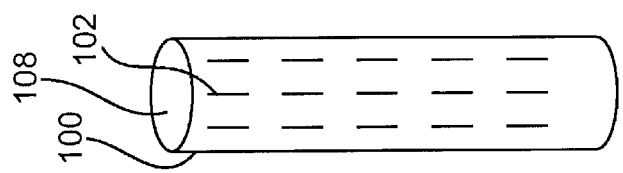
FIG. 8 shows the primary fenestrated endovascular graft of FIG. 7 with another pattern of perforation.

FIG. 8 shows the primary fenestrated endovascular graft 100 of FIG. 7 with another pattern of perforations 102.

Figure 9:
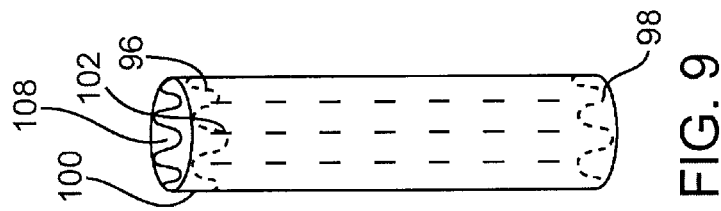
FIG. 9 shows the primary fenestrated endovascular graft of FIG. 7 with another pattern of perforation.

FIG. 9 shows the primary fenestrated endovascular graft 100 of FIG. 7 with another pattern of perforations 102. By way of example, the primary fenestrated endovascular graft 100 of FIG. 9 is shown as a stented graft, with a proximal stent 96 and a distal stent 98 for fixation of the proximal and distal ends of the graft within the aorta. The stents 96, 98 may be constructed of a highly elastic material so that they will be self-expanding or they may be constructed of a malleable material for balloon expansion of the graft.

Figure 10:
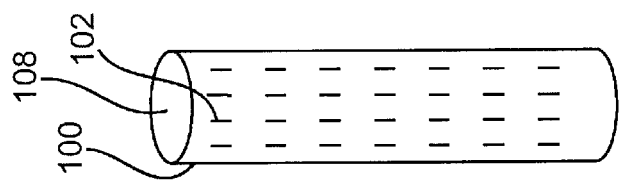
FIG. 10 shows the primary fenestrated endovascular graft of FIG. 7 with another pattern of perforation.

FIG. 10 shows the primary fenestrated endovascular graft 100 of FIG. 7 with another pattern of perforations 102.

Figure 11:
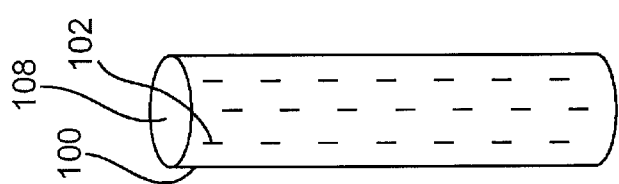
FIG. 11 shows the primary fenestrated endovascular graft of FIG. 7 with yet another pattern of perforation.

FIG. 11 shows the primary fenestrated endovascular graft 100 of FIG. 7 with yet another pattern of perforations 102.

Figure 12:
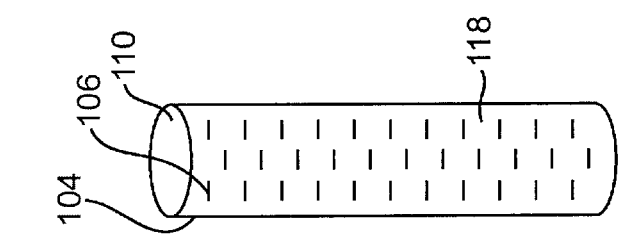

A second layer of endovascular graft may be utilized in concert with the primary layer. FIG. 12 shows the secondary fenestrated endovascular graft 104 for use in conjunction with the primary fenestrated endovascular graft 100 of FIG. 7. The secondary fenestrated endovascular graft 104 is generally tubular in shape with a central lumen 110. This secondary layer 104 will be fixed either primarily or secondarily to the vascular wall such that its fixation is based on a transmural mechanism, i.e. it may itself have fixation transmurally to the vessel wall or positive fixation to another graft that has transmural wall fixation. This secondary layer 104 will serve to seal the fenestrations 102 of the primary graft layer 100 where desired. It will be penetrable by guidewires. The primary and secondary fenestrated endovascular grafts 100, 104 may or may not be malleable such that transgraft passage by a guidewire would allow expansion of the passage to larger diameters with a dilating device such a balloon, dilator or cutters. The primary and secondary fenestrated endovascular grafts 100, 104 will be interchangeable with respect to their radial proximity to the vascular wall, i.e. one or the other may be placed first or second.

The secondary fenestrated endovascular graft 104 may also be made of polyester, polytetrafluoroethylene (PTFE) or any other suitable fabric. Likewise, the secondary fenestrated endovascular graft 104 may be reinforced or unreinforced and stented or nonstented. The secondary fenestrated endovascular graft 104 will also have a multiplicity of fenestrations or perforations 106, which are preferably in the form of slits 2–15 mm long space at different intervals with either constant or varying distance between the slits. The slits 106 will be oriented longitudinally, horizontally (i.e. circumferentially) or at an angle with respect to the axis of the graft, or in any combination thereof. Preferably, the slits 106 in the secondary fenestrated endovascular graft 104 will be oriented at a different angle than the slits 102 of the primary fenestrated endovascular graft 100 so that the walls of the two layers will overlap to occlude the slits 102, 104 when deployed concentrically. The perforations or slits 106 may pass all the way through the wall 118 of the secondary fenestrated endovascular graft 104 or they may be thinner or weaker areas in the wall 116 to facilitate piercing the secondary fenestrated endovascular graft 104. Alternatively, the secondary fenestrated endovascular graft 104 may be made of a micromesh fabric with small holes that are guidewire accessible and dilatable.

In an alternative embodiment, the primary and secondary fenestrated endovascular grafts 100, 104 may be permanently nested together to form a two-layered endovascular graft device.

Figures 13, 14, 15, 16:
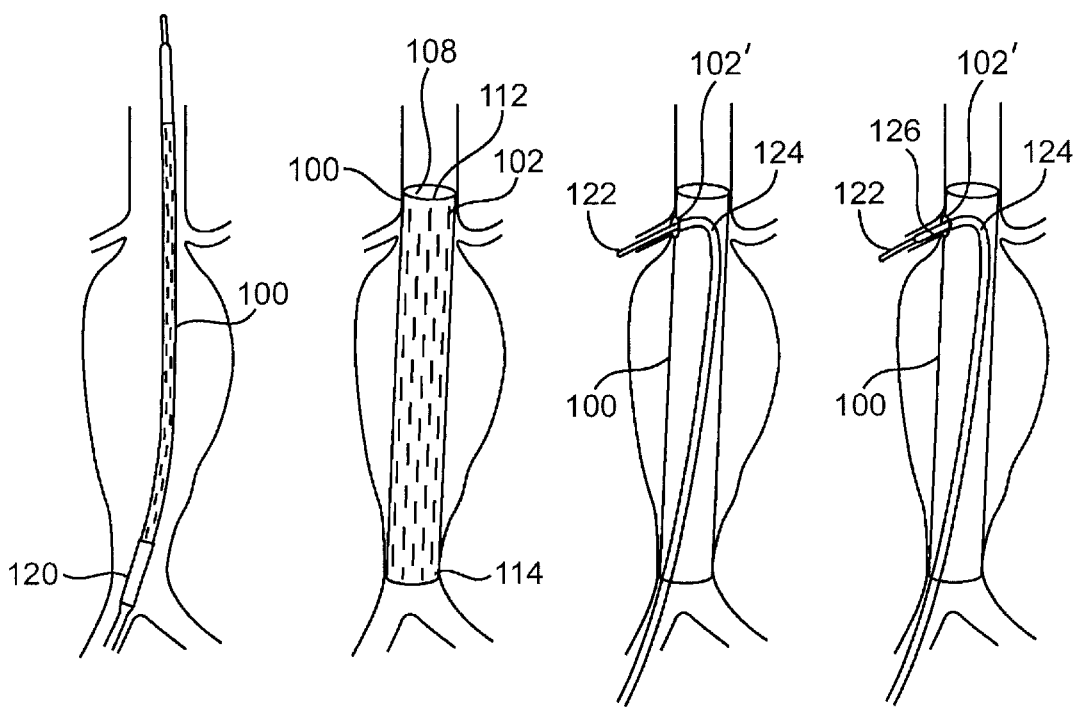
FIG. 13 shows the primary fenestrated endovascular graft being introduced over a catheter into an abdominal aortic aneurysm in a patient's aorta.
FIG. 14 shows the primary fenestrated endovascular graft expanded to exclude the abdominal aortic aneurysm.
FIG. 15 shows a guidewire introduced through a guiding catheter to pierce the primary fenestrated endovascular graft at the ostium of the right renal artery.
FIG. 16 shows a balloon catheter introduced through the guiding catheter to expand the opening through the primary fenestrated endovascular graft at the ostium of the right renal artery.

FIG. 13 shows the primary fenestrated endovascular graft 100 being introduced over a catheter 120 into an abdominal aortic aneurysm in a patient's aorta. The primary fenestrated endovascular graft 100 is preferably fixed in a normal part of aorta proximal to the section to be repaired or excluded. Typically, this will be in the lower thoracic aorta for all abdominal pathology and proximal to the innominate artery for the thoracic pathology, although fixation can be placed at any normal diameter aorta with suitable mural morphology for the fixation technique. The proximal or upstream end 112 of the primary fenestrated endovascular graft 100 may be placed proximal or superior to any or all of the renal, hepatic and mesenteric arteries when appropriate.

FIG. 14 shows the primary fenestrated endovascular graft 100 expanded to exclude the abdominal aortic aneurysm. The primary fenestrated endovascular graft 100 may be self-expanding or it may be balloon expandable, or a combination of the two techniques may be used. The proximal or upstream end 112 of the primary fenestrated endovascular graft 100 is shown placed in a suprarenal position. The distal or downstream end 114 of the primary fenestrated endovascular graft 100 may be placed in the distal abdominal aorta, as shown, or it may be placed in the iliac or femoral arteries in the case of a bifurcated endovascular graft.

The primary fenestrated endovascular graft 100 may then be pierced or perforated by various methods to facilitate making a fluid connection or anastomosis with one or more of the sidebranches of the vessel into which it is implanted. By way of example, FIG. 15 shows a guidewire 122 introduced through a guiding catheter 124 to pierce the primary fenestrated endovascular graft 100 at the ostium of the right renal artery. The guidewire 122 will typically pass through one of the slits 102' in the graft wall.

FIG. 16 shows a balloon catheter 126 introduced through the guiding catheter 124 to expand the opening or fenestration 102' through the primary fenestrated endovascular graft 100 at the ostium of the right renal artery. If the primary fenestrated endovascular graft 100 is made of a malleable material, dilating the opening(s) 102' through the graft may be sufficient for making a fluid connection with the tributary vessels or sidebranches of the aorta.

Figures 17, 18, 19, 20:
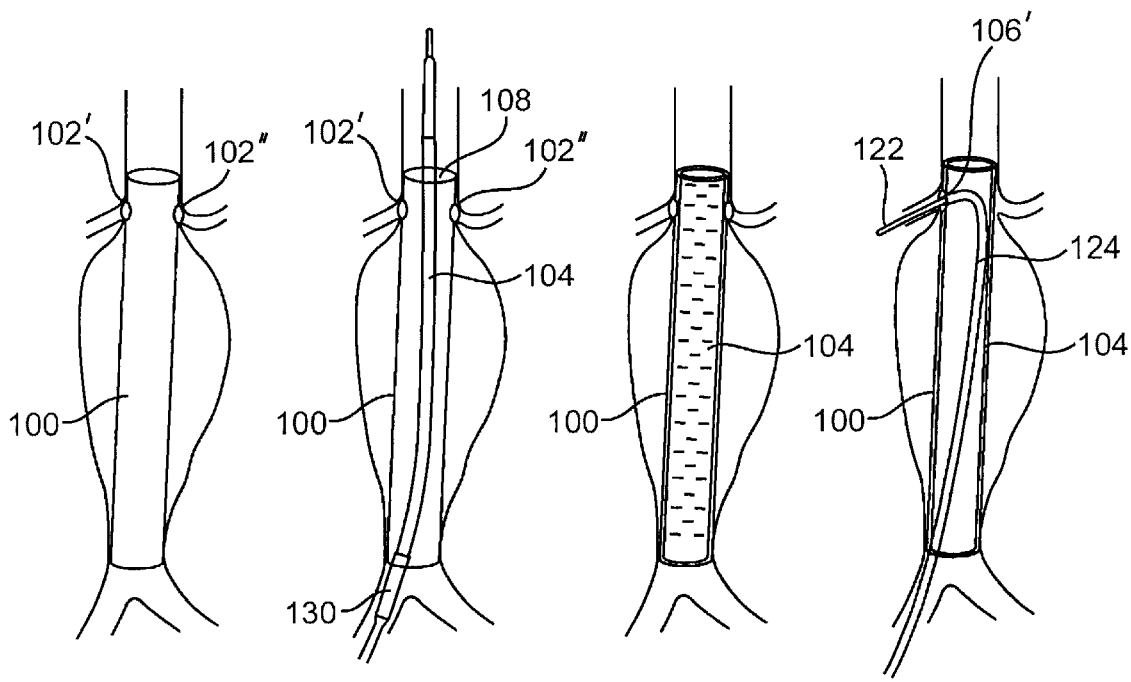
FIG. 17 shows the primary fenestrated endovascular graft fully implanted with the catheters withdrawn.
FIG. 18 shows the secondary fenestrated endovascular graft being introduced over a catheter into the primary fenestrated endovascular graft.
FIG. 19 shows the secondary fenestrated endovascular graft expanded within the primary fenestrated endovascular graft.
FIG. 20 shows a guidewire introduced through a guiding catheter to pierce the secondary fenestrated endovascular graft at the ostium of the right renal artery.

FIG. 17 shows the primary fenestrated endovascular graft 100 fully implanted with the catheters withdrawn. A first opening 102' has been made for the right renal artery and a second opening 102" has been made for the left renal artery.

Optionally, a secondary fenestrated endovascular graft 104 may be implanted within the lumen 108 of the primary fenestrated endovascular graft 100. FIG. 18 shows the secondary fenestrated endovascular graft 104 being introduced over a catheter 130 into the lumen 108 of the primary fenestrated endovascular graft 100.

FIG. 19 shows the secondary fenestrated endovascular graft 104 expanded within the primary fenestrated endovascular graft 100. The secondary fenestrated endovascular graft 104 may be self-expanding or it may be balloon expandable, or a combination of the two techniques may be used.

FIG. 20 shows a guidewire 122 introduced through a guiding catheter 124 to pierce the secondary fenestrated endovascular graft 104 at the ostium of the right renal artery. The guidewire 122 will typically pass through one of the slits 106' in the graft wall in alignment with the fenestration 102' in the primary fenestrated endovascular graft 100.

Figures 21, 22, 23, 24:
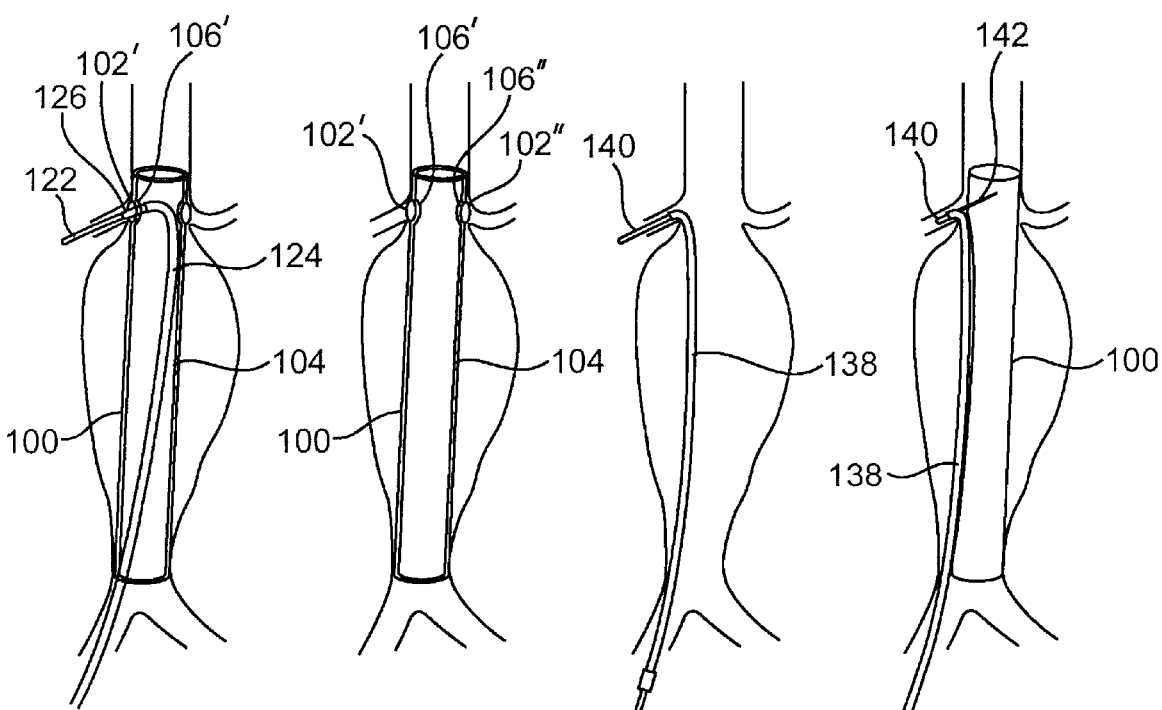
FIG. 21 shows a balloon catheter introduced through the guiding catheter to expand the opening through the secondary fenestrated endovascular graft at the ostium of the right renal artery.
FIG. 22 shows the primary and secondary fenestrated endovascular grafts fully implanted with the catheters withdrawn.
FIG. 23 shows a guidewire with a piercing element introduced through a catheter into the right renal artery prior to introduction of the fenestrated endovascular graft.
FIG. 24 shows the catheter withdrawn to expose the piercing element. The guidewire is withdrawn proximally, causing the piercing element to perforate the fenestrated endovascular graft at the ostium of the right renal artery.

FIG. 21 shows a balloon catheter 126 introduced through the guiding catheter to expand the opening or fenestration 106' through the secondary fenestrated endovascular graft 104 at the ostium of the right renal artery. The steps of piercing or penetrating the primary and secondary fenestrated endovascular grafts 100, 104 may be done separately, as illustrated, or both grafts 100, 104 may be implanted and the fenestrations 102', 106' through both graft layers may be formed at the same time.

FIG. 22 shows the primary and secondary fenestrated endovascular grafts 100, 104 fully implanted with the catheters withdrawn. A first opening 102', 106' has been made through the primary and secondary fenestrated endovascular grafts 100, 104 for the right renal artery, and a second opening 102", 106" has been made through the primary and secondary fenestrated endovascular grafts 100, 104 for the left renal artery.

Alternatively or in conjunction with the guiding catheter and guidewire technique of FIGS. 15 and 20, a special guidewire 140 with a retrograde or rearwardly-facing piercing element 142 may be used to pierce the primary and/or secondary fenestrated endovascular grafts 102, 104 to form the fenestrations at the ostia of the sidebranches. Preferably, the guidewire 140 is constructed with a flexible distal portion 144 and a relatively stiffer proximal portion 146, with the rearwardly-facing piercing element 142 mounted in the vicinity of the flexible distal portion 144. FIG. 23 shows the special guidewire 140 with a piercing element 142 introduced through a catheter 138 into the right renal artery prior to introduction of the fenestrated endovascular graft. The piercing element 142 is within the catheter 138 and, therefore, not visible in this view.

FIG. 24 shows the catheter 138 withdrawn to expose the piercing element 142. The guidewire 140 is withdrawn proximally, causing the piercing element 142 to perforate the fenestrated endovascular graft 100 at the ostium of the right renal artery.

Figure 25:
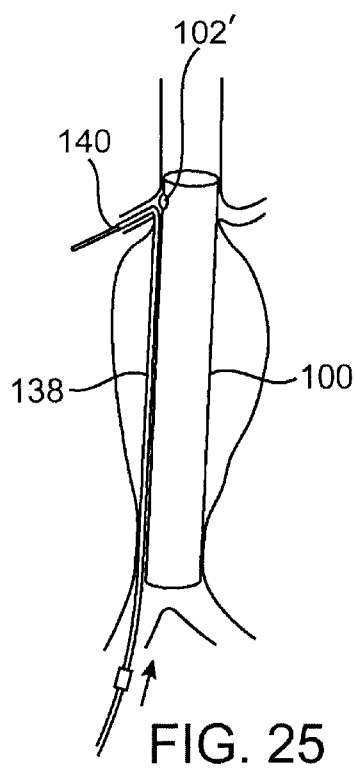
FIG. 25 shows the catheter advanced to cover the piercing element for removal from the patient.

FIG. 25 shows the guidewire 140 advanced distally to retract the piercing element 142 and the catheter 138 advanced to cover the piercing element 142 for removal from the patient. An opening 102' has been formed in the fenestrated endovascular graft 100 at the ostium of the right renal artery.

Figure 27:
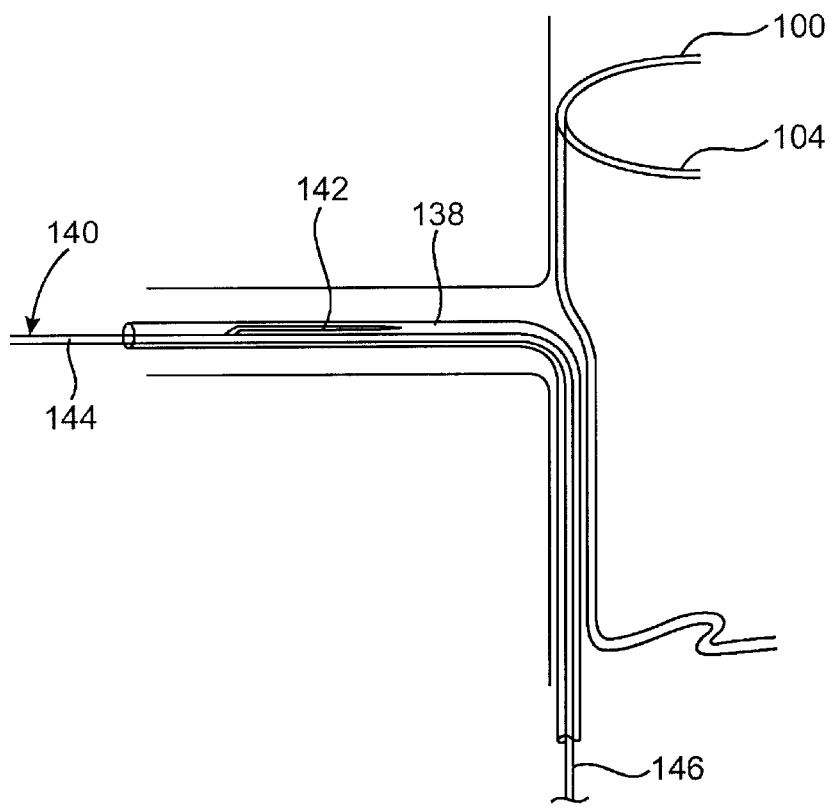
FIG. 27 is an enlarged view of the guidewire with a piercing element introduced through a catheter into a sidebranch of the aorta and with the fenestrated endovascular graft expanded within the aorta.

FIG. 27 is an enlarged view of the guidewire 140 with a piercing element 142 introduced through a catheter 138 into a sidebranch of the aorta and with the fenestrated endovascular graft 100, 104 expanded within the aorta.

Figure 28:
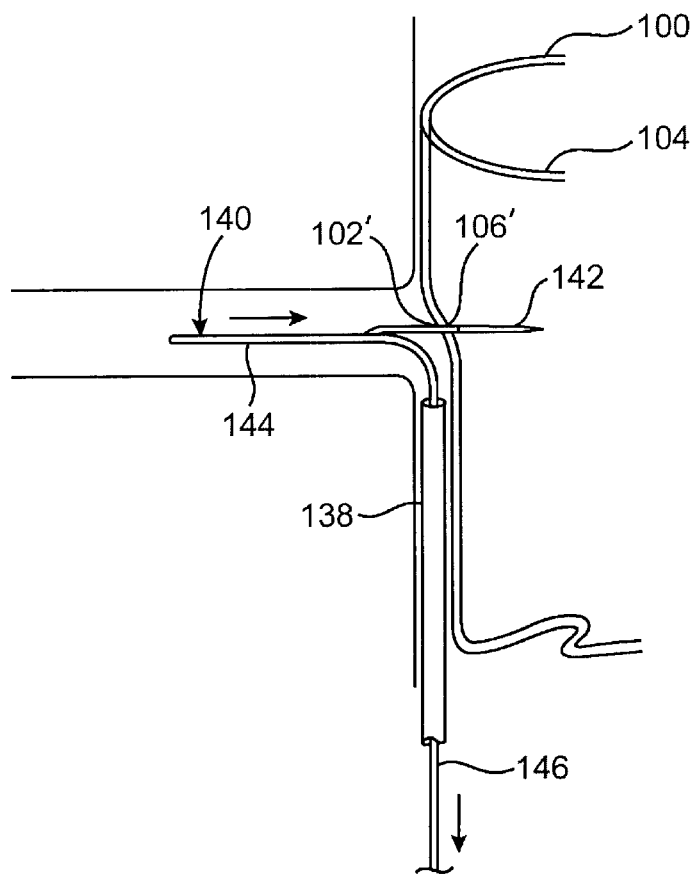
FIG. 28 is an enlarged view showing the guidewire withdrawn proximally, causing the piercing element to perforate the fenestrated endovascular graft at the ostium of the sidebranch.

FIG. 28 is an enlarged view showing the guidewire 140 withdrawn proximally, causing the piercing element 142 to perforate the fenestrated endovascular graft 100, 104 at the ostium of the sidebranch.

The steps of piercing or penetrating the primary and secondary fenestrated endovascular grafts 100, 104 may be done separately, as shown in FIGS. 23–25, or both grafts 100, 104 may be implanted and the fenestrations 102', 106' through both graft layers may be formed at the same time, as shown in FIGS. 27–28. These techniques may be used with each of the tributary vessels or sidebranches of the aorta, including the renal, hepatic and mesenteric arteries.

Figure 26:
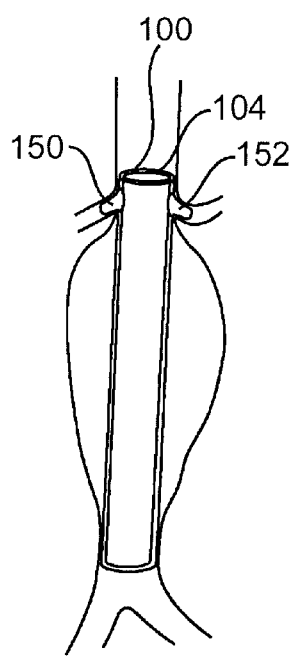
FIG. 26 shows the primary and secondary fenestrated endovascular grafts implanted in the aorta with sidebranch stents implanted in the renal ostia to maintain a fluid connection between the aortic lumen and the renal arteries.

FIG. 26 shows the primary and secondary fenestrated endovascular grafts 100, 104 implanted in the aorta with optional sidebranch stents 150, 152 implanted in the renal ostia to maintain a fluid connection between the aortic lumen and the renal arteries. The sidebranch stents 150, 152 may be self-expanding or balloon expandable, or a combination of the two techniques may be used. The sidebranch stents 150, 152 may be bare stents or covered stents.

Figure 29:
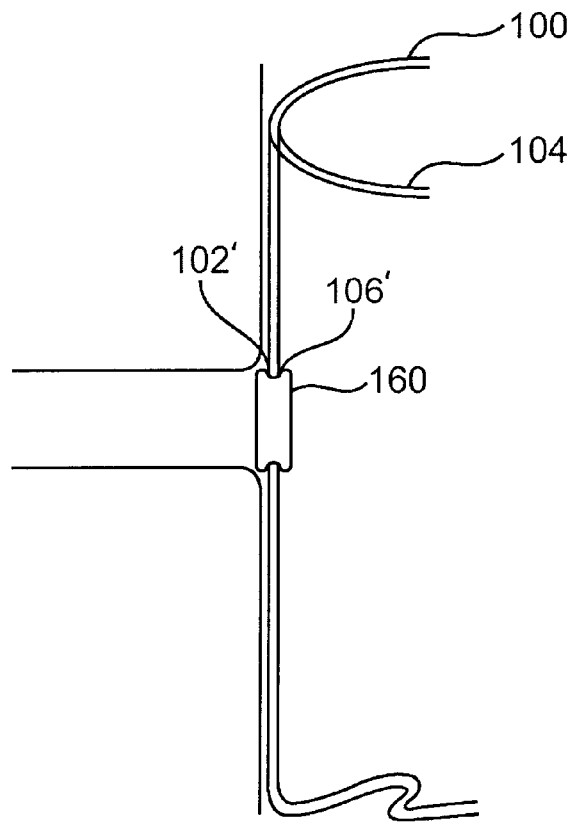
FIG. 29 is an enlarged view showing the primary and secondary fenestrated endovascular grafts implanted in the aorta with a flange or grommet inserted into the opening in the wall of the fenestrated endovascular graft to maintain a fluid connection between the aortic lumen and the lumen of the sidebranch.

FIG. 29 is an enlarged view showing the primary and secondary fenestrated endovascular grafts 100, 104 implanted in the aorta with a flange or grommet 160 inserted into the opening in the wall of the fenestrated endovascular graft to maintain a fluid connection between the aortic lumen and the lumen of the sidebranch. The flange 160 or grommet may be self-expanding or it may be balloon expandable, or a combination of the two techniques may be used.

Figure 30:
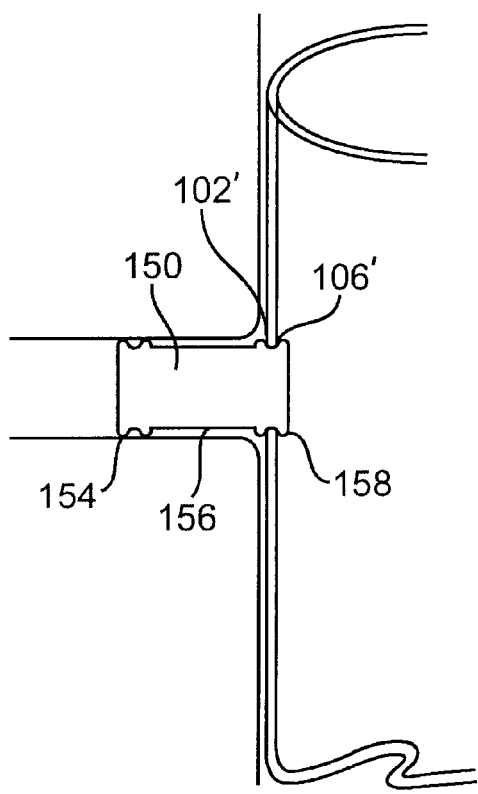
FIG. 30 is an enlarged view showing the primary and secondary fenestrated endovascular grafts implanted in the aorta with a sidebranch stent implanted in the ostium of the sidebranch to maintain a fluid connection between the aortic lumen and the lumen of the sidebranch.

FIG. 30 is an enlarged view showing the primary and secondary fenestrated endovascular grafts 100, 104 implanted in the aorta with a sidebranch stent 150 implanted in the ostium of the sidebranch to maintain a fluid connection between the aortic lumen and the lumen of the sidebranch. In this exemplary embodiment, the sidebranch stent 150 is made with a flange or flanges 158 on the proximal end to create a fluid seal with the walls of the primary and secondary fenestrated endovascular grafts 100, 104. The distal end of the sidebranch stent 150 has an expandable anchor 154 to create a fluid seal with the walls of the sidebranch vessel. The body 156 of the sidebranch stent 150 between the expandable anchor 154 on the distal end and the flanges 158 on the proximal end may be flexible or expandable to allow for relative movement between the primary and secondary fenestrated endovascular grafts 100, 104 and the sidebranch vessel.

In an alternative method, the primary and secondary fenestrated endovascular grafts 100, 104 may be permanently nested together to form a two-layered endovascular graft device. The primary and secondary fenestrated endovascular grafts 100, 104 are delivered mounted on a single catheter 120 and implanted simultaneously in the aorta, similar to the method shown in FIGS. 13–14. Then, the fenestrations 102', 106' and 102", 106" and anastomoses with the branch vessels may be formed by any of the methods described above.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof. For example, although specific examples have been described for treatment of thoracic and abdominal aortic aneurysms, the apparatus and methods described herein are also applicable to other vessels of the body, including other arteries, veins and other body passages.

What is claimed is:

1. A fenestrated endovascular graft, comprising:
    an outer tubular graft body having a graft wall surrounding a central lumen and a multiplicity of fenestrations through the graft wall, wherein the fenestrations through the outer graft wall are in the form of slits oriented longitudinally with respect to the outer tubular graft body; and
    an inner tubular graft body sized and configured for placement within the central lumen of the outer tubular graft body, the inner tubular graft body having a graft wall surrounding a central lumen and a multiplicity of fenestrations through the graft wall, wherein the fenestrations through the inner graft wall are in the form of slits oriented circumferentially with respect to the inner tubular graft body.

2. The fenestrated endovascular graft of claim 1, further comprising:
    at least one expandable stent connected to the outer tubular graft body or the inner tubular graft body.

3. The fenestrated endovascular graft of claim 1, wherein the fenestrations through the outer tubular graft body and the fenestrations through the inner tubular graft body are expandable.

4. The fenestrated endovascular graft of claim 1, wherein the outer tubular graft body and the inner tubular graft body are permanently attached to one another.

5. The fenestrated endovascular graft of claim 1, wherein the outer tubular graft body and the inner tubular graft body are separable from one another.

6. The fenestrated endovascular graft of claim 1, wherein the fenestrations through the outer graft wall are configured to seal against the inner graft wall and the fenestrations through the inner graft wall are configured to seal against the outer graft wall when the inner tubular graft body is placed within the central lumen of the outer tubular graft body.

7. The fenestrated endovascular graft of claim 1, further comprising:
    a grommet insertable into an opening formed through the outer graft wall and the inner graft wall.

8. The fenestrated endovascular graft of claim 1, further comprising:
    a sidebranch graft connectable to an opening formed through the outer graft wall and the inner graft wall.

9. The fenestrated endovascular graft of claim 8, wherein the sidebranch graft has a flange configured to form a fluidtight connection to the opening through the outer graft wall and the inner graft wall and an expandable anchor configured to form a fluidtight seal with a branch vessel.

10. The fenestrated endovascular graft of claim 1, wherein the fenestrated endovascular graft is part of a kit including:
    a graft delivery catheter for implanting the fenestrated endovascular graft within a patient's blood vessel; and
    a guidewire for forming the opening in the graft wall.

11. The fenestrated endovascular graft of claim 10, wherein the guidewire includes a rearwardly-facing piercing element.

12. The fenestrated endovascular graft of claim 11, wherein the kit further comprises a catheter for introducing the guidewire into the patient's blood vessel.

13. A method of repairing a patient's blood vessel, comprising:
    inserting an outer tubular graft body into the blood vessel, the outer tubular graft body having a graft wall surrounding a central lumen and a multiplicity of longitudinally oriented fenestrations through the graft wall; and
    inserting an inner tubular graft body into the central lumen of the outer tubular graft body, the inner tubular graft body having a graft wall surrounding a central lumen and a multiplicity of circumferentially oriented fenestrations through the graft wall.

14. The method of claim 13, wherein the fenestrations through the outer graft wall are configured to seal against the inner graft wall and the fenestrations through the inner graft wall are configured to seal against the outer graft wall when the inner tubular graft body is placed within the central lumen of the outer tubular graft body.

15. The method of claim 13, further comprising:
    forming an opening through the graft wall of the outer tubular graft body and the graft wall of the inner tubular graft body in the vicinity of an ostium of a branch vessel.

16. The method of claim 15, further comprising:
    inserting a grommet into the opening through the graft wall of the outer tubular graft body and the graft wall of the inner tubular graft body.

17. The method of claim 15, further comprising:
    inserting a sidebranch graft into the opening through the graft wall of the outer tubular graft body and the graft wall of the inner tubular graft body.

18. The method of claim 17, further comprising:
    forming a fluidtight connection between the sidebranch graft and the opening through the outer graft wall and the inner graft wall; and
    forming a fluidtight connection between the sidebranch graft and the branch vessel.

* * * * *

UNITED STATES PATENT AND TRADEMARK OFFICE
CERTIFICATE OF CORRECTION

PATENT NO. : 6,652,567 B1  
DATED : November 25, 2003  
INVENTOR(S) : Deaton, David H.

It is certified that error appears in the above-identified patent and that said Letters Patent is hereby corrected as shown below:

<u>Column 9,</u>
Line 50, please change "body." to read as follows:
-- body;
wherein at least one fenestration through the outer graft wall is aligned with at least one fenestration through the inner graft wall at a point where it is desired to create an opening though the endovascular graft. --

<u>Column 10,</u>
Line 39, please change "body." to read as follows:
-- body; and
aligning at least one fenestration through the outer graft wall with at least one fenestration through the inner graft wall at a point where it is desired to create an opening though the endovascular graft. --

Signed and Sealed this

Fourth Day of May, 2004

JON W. DUDAS
*Acting Director of the United States Patent and Trademark Office*